United States Patent
Peng et al.

(10) Patent No.: US 11,964,929 B2
(45) Date of Patent: Apr. 23, 2024

(54) APPLICATION OF GLUTAMINE DERIVATIVE IN PREPARATION OF ANIMAL FEED ADDITIVE

(71) Applicant: Xianfeng Peng, Guangdong (CN)

(72) Inventors: Xianfeng Peng, Guangzhou (CN); Huacheng Huang, Guangzhou (CN)

(73) Assignee: WISORIG TECHNOLOGIES PTE. LIMITED (SG)

( * ) Notice: Subject to any disclaimer, the term of this patent is extended or adjusted under 35 U.S.C. 154(b) by 428 days.

(21) Appl. No.: 17/311,311

(22) PCT Filed: Dec. 18, 2018

(86) PCT No.: PCT/CN2018/121709
§ 371 (c)(1),
(2) Date: Jun. 4, 2021

(87) PCT Pub. No.: WO2020/124351
PCT Pub. Date: Jun. 25, 2020

(65) Prior Publication Data
US 2022/0024859 A1    Jan. 27, 2022

(51) Int. Cl.
| | |
|---|---|
| C07C 237/42 | (2006.01) |
| A23K 20/142 | (2016.01) |
| A23K 50/30 | (2016.01) |
| A23K 50/75 | (2016.01) |
| A23K 50/80 | (2016.01) |
| C07D 295/195 | (2006.01) |

(52) U.S. Cl.
CPC .......... *C07C 237/42* (2013.01); *A23K 20/142* (2016.05); *A23K 50/30* (2016.05); *A23K 50/75* (2016.05); *A23K 50/80* (2016.05); *C07D 295/195* (2013.01)

(58) Field of Classification Search
CPC ............................. C07C 237/42; A23K 20/142
See application file for complete search history.

(56) References Cited

U.S. PATENT DOCUMENTS

| | | | |
|---|---|---|---|
| 4,791,215 A | 12/1988 | Rovati et al. | |
| 2005/0100572 A1 | 5/2005 | Hatajima et al. | |
| 2006/0217321 A1* | 9/2006 | Ozeki ..................... | A61P 25/00 514/17.7 |
| 2017/0258122 A1 | 9/2017 | Elings et al. | |

FOREIGN PATENT DOCUMENTS

| | | |
|---|---|---|
| CN | 101760499 A | 6/2010 |
| CN | 108041286 A | 5/2018 |

OTHER PUBLICATIONS

International Search Report of PCTCN2018121709, dated Sep. 17, 2019.
English Translation of International Search Report of PCTCN2018121709.
Makovec, F., "New glutamic and aspartic derivatives with potent CCK-antagonistic activity," European Journal of Medicinal Chemistry, vol. 21, p. 9-20, Dec. 31, 1986(Dec. 31, 1986).
Ekborg-Ott, K. H., "Avoparcin, a new macrocyclic antibiotic chiral run buffer additive for capillary electrophoresis," Electrophoresis, vol. 12, p. 2348-2457, Dec. 31, 1999 (Dec. 31, 1999).
Tamura, K., "Dual G1 and G2/M phase inhibitor by SC-αα δ9, a combinatorially derived Cdc25 phosphatase inhibitor," Oncogene, vol. 18, p. 6989-6996, Nov. 30, 1999 (Nov. 30, 1999).
Conde, S., "Regioselective lipase-catalysed γ-monoamidation of D-glutamic acid diesters: effect of the N-protecting group," Tetrahedron: Asymmetry, vol. 11, p. 2537-2545, Dec. 31, 2000 (Dec. 31, 2000).
English Translation of CN108041286A.
English Translation of CN101760499A.

* cited by examiner

*Primary Examiner* — Changqing Li
(74) *Attorney, Agent, or Firm* — Kam Wah Law

(57) ABSTRACT

The present invention provides the use of a glutamine derivative in preparing animal feed additives, and particularly the use of a glutamine derivative having a structure of formula (I), a racemate thereof, a stereoisomer thereof, a geometric isomer thereof, a tautomer thereof, a solvate thereof, or a feed acceptable salt thereof. Animal breeding experiments revealed that, the provided compounds, including the glutamine derivative, the racemate thereof, the stereoisomer thereof, the geometric isomer thereof, the tautomer thereof, the solvate thereof, and the feed acceptable salt thereof, can be used as animal feed additives, exhibiting excellent effect in improving animal production performance such as growth and feed efficiency.

Formula (I)

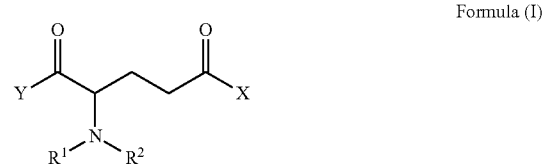

20 Claims, No Drawings

APPLICATION OF GLUTAMINE DERIVATIVE IN PREPARATION OF ANIMAL FEED ADDITIVE

CROSS REFERENCE TO RELATED APPLICATION

This is a U.S. national stage application of the International Patent Application No. PCT/CN2018/121709, filed Dec. 18, 2018, which is incorporated herein by reference in its entirety.

TECHNICAL FIELD

The present invention relates to the field of animal feed additives, and particularly relates to the use of a glutamine derivative, a racemate thereof, a stereoisomer thereof, a geometric isomer thereof, a tautomer thereof, a solvate thereof, or a feed acceptable salt thereof, in preparing animal feed additives; the present invention also relates to a feed composition comprising the glutamine derivative, the racemate thereof, the stereoisomer thereof, the geometric isomer thereof, the tautomer thereof, the solvate thereof, or the feed acceptable salt thereof, and further relates to the use of the feed composition in preparing animal feed additives or animal feeds.

BACKGROUND

Generally, aminoacylated glutamine derivatives are intermediates during the production of amide-substituted derivatives of glutamine. It has been reported that N-acetyl-DL-theanine was reacted with Aspergillus oryzae aminoacylase to give L-theanine under suitable conditions. It has also been reported that L-glutamic acid was reacted with phthalic anhydride to give phthaloyl-L-glutamic acid which then turns into acid anhydride; the acid anhydride is subjected to ammonolysis in an ethylamine aqueous solution to give phthaloyl-L-theanine, and then L-theanine is obtained by removing the phthaloyl group of phthaloyl-L-theanine in the presence of hydrazine hydrate.

Aminoacylated glutamine derivatives can synergistically enhance sensory performance. It has been reported that the aqueous solution of N-acyl theanine has disappointingly weak fatty taste, but it is possible to supplement, enhance or strengthen the basic or true fragrance and taste of food/beverage by combining this compound with flavoring matters and carefully adjusting their levels.

Feed additives, refer to substances added in small or trace amounts during feed processing, production, and application, including nutritive feed additives and general feed additives. The general feed additives refer to substances added in small or trace amount in feed for guaranteeing or improving feed quality and increasing feed utilization. At present, commonly used general feed additives that can efficiently and stably increase feed utilization and improve animal production performance mainly include: high-level copper agents, high-level zinc agents, feed antibiotics, and chemically synthesized antibacterial agents. However, the long-term use of these substances in the husbandry will lead to great side effects, such as animal liver and kidney toxicity, growth inhibition, kidney damage, urinary tract disorders, teratogenesis, mutagenesis, drug resistance, drug residues, and environmental pollution. In order to guarantee animal health and improve the production efficiency of the husbandry, it is an urgent need to develop novel feed additives that are effective, stable and safe.

SUMMARY

In view of the above, the present invention provides the use of a glutamine derivative, a racemate thereof, a stereoisomer thereof, a geometric isomer thereof, a tautomer thereof, a solvate thereof, or a feed acceptable salt thereof, in preparing animal feed additives; the present invention also provides a feed composition comprising the glutamine derivative, the racemate thereof, the stereoisomer thereof, the geometric isomer thereof, the tautomer thereof, the solvate thereof, or the feed acceptable salt thereof, and further provide the use of the feed composition in preparing animal feed additives or animal feeds.

In one aspect, provided herein is a glutamine derivative having a structure of formula (I), a racemate thereof, a stereoisomer thereof, a geometric isomer thereof, a tautomer thereof, a solvate thereof, or a feed acceptable salt thereof, for use in preparing an animal feed additive:

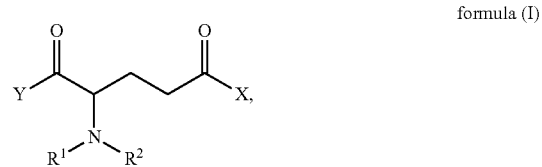

formula (I)

wherein, Y is an $OC_1$-$C_{20}$ alkyl group or OH; X is a nitrogen-containing $C_4$-$C_{10}$ cycloalkyl group, a $NHC_1$-$C_{20}$ alkyl group, or a $N(C_1$-$C_{20}$ alkyl group$)_2$; $R^1$ is $R^{1a}C(=O)$, $R^{1b}C(=O)$, $R^{1a}S(=O)_2$, $R^{1b}S(=O)_2$, or H; $R^2$ is $R^{2a}C(=O)$, $R^{2b}C(=O)$, $R^{2a}S(=O)_2$, or $R^{2b}S(=O)_2$;

each of $R^{1b}$ and $R^{2b}$ is independently a $C_1$-$C_{20}$ alkyl group, a $C_3$-$C_7$ cycloalkyl group, or a $C_1$-$C_{20}$ alkyl group or $C_3$-$C_7$ cycloalkyl group optionally substituted with one, two, three, four, or five $R^3$;

$R^3$ is —OH, —$NH_2$, —CN, —SH, or —$X_1$, wherein $X_1$ is selected from F, Cl, Br, or I;

each of $R^{1a}$ and $R^{2a}$ is independently a $C_5$-$C_{12}$ aryl group, a $C_5$-$C_{12}$ heteroaryl group, a —($C_1$-$C_4$ alkylidene)-$C_5$-$C_{12}$ aryl group, a —($C_1$-$C_4$ alkylidene)-$C_5$-$C_{12}$ heteroaryl group or, a $C_5$-$C_{12}$ aryl group, $C_5$-$C_{12}$ heteroaryl group, —($C_1$-$C_4$ alkylidene)-$C_5$-$C_{12}$ aryl group or —($C_1$-$C_4$ alkylidene)-$C_5$-$C_{12}$ heteroaryl group, optionally substituted with one, two, three, four, or five $R^4$;

$R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In another aspect, provided herein is a feed composition, wherein the feed composition comprises at least one of the glutamine derivative of formula (I), the racemate thereof, the stereoisomer thereof, the geometric isomer thereof, the tautomer thereof, the solvate thereof, and the feed acceptable salt thereof, according to claim 1, and an adjuvant suitable for feeds.

In another aspect, provided herein is a feed composition disclosed herein for use in preparing an animal feed additive or an animal feed.

DETAILED DESCRIPTION OF THE INVENTION

In one aspect, the present invention provides a glutamine derivative having a structure of formula (I), a racemate thereof, a stereoisomer thereof, a geometric isomer thereof, a tautomer thereof, a solvate thereof, or a feed acceptable salt thereof.

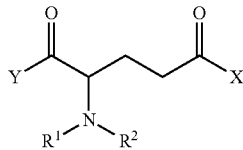

Formula (I)

In some technical solutions, Y is an $OC_1$-$C_{20}$ alkyl group or OH; X is a nitrogen-containing $C_4$-$C_{10}$ cycloalkyl group, a $NHC_1$-$C_{20}$ alkyl group or a $N(C_1$-$C_{20}$ alkyl group$)_2$; $R^1$ is $R^{1a}C(=O)$, $R^{1b}C(=O)$, $R^{1a}S(=O)_2$, $R^{1b}S(=O)_2$ or H; $R^2$ is $R^{2a}C(=O)$, $R^{2b}C(=O)$, $R^{2a}S(=O)_2$ or $R^{2b}S(=O)_2$; each of $R^{1b}$ and $R^{2b}$ is independently a $C_1$-$C_{20}$ alkyl group, a $C_3$-$C_7$ cycloalkyl group or, a $C_1$-$C_{20}$ alkyl group or $C_3$-$C_7$ cycloalkyl group, optionally substituted with one, two, three, four, or five $R^3$; wherein $R^3$ is —OH, —$NH_2$, —CN, —SH, or —$X_1$, wherein $X_1$ is selected from F, Cl, Br, or I; each of $R^{1a}$ and $R^{2a}$ is independently a $C_5$-$C_{12}$ aryl group, a $C_5$-$C_{12}$ heteroaryl group, a —($C_1$-$C_4$ alkylidene)-$C_5$-$C_{12}$ aryl group, a —($C_1$-$C_4$ alkylidene)-$C_5$-$C_{12}$ heteroaryl group or, a $C_5$-$C_{12}$ aryl group, a $C_5$-$C_{12}$ heteroaryl group, a —($C_1$-$C_4$ alkylidene)-$C_5$-$C_{12}$ aryl group or a —($C_1$-$C_4$ alkylidene)-$C_5$-$C_{12}$ heteroaryl group, optionally substituted with one, two, three, four, or five $R^4$; wherein $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In some technical solutions, $R^1$ is $R^{1a}C(=O)$ or H; $R^2$ is $R^{2a}C(=O)$; each of $R^{1a}$ and $R^{2a}$ is independently a $C_5$-$C_{12}$ aryl group, a $C_5$-$C_{12}$ heteroaryl group, a —($C_1$-$C_4$ alkylidene)-$C_5$-$C_{12}$ aryl group, a —($C_1$-$C_4$ alkylidene)-$C_5$-$C_{12}$ heteroaryl group or, a $C_5$-$C_{12}$ aryl group, a $C_5$-$C_{12}$ heteroaryl group, a —($C_1$-$C_4$ alkylidene)-$C_5$-$C_{12}$ aryl group or a —($C_1$-$C_4$ alkylidene)-$C_5$-$C_{12}$ heteroaryl group, optionally substituted with one, two, three, four, or five $R^4$; wherein $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In some technical solutions, $R^1$ is H; $R^2$ is $R^{2a}C(=O)$; $R^{2a}$ is a $C_5$-$C_{12}$ aryl group, a —($C_1$-$C_4$ alkylidene)-$C_5$-$C_{12}$ aryl group or, a $C_5$-$C_{12}$ aryl group or a —($C_1$-$C_4$ alkylidene)-$C_5$-$C_{12}$ aryl group, optionally substituted with one, two, three, four, or five $R^4$; wherein $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In some technical solutions, $R^1$ is H; $R^2$ is $R^{2a}C(=O)$; $R^{2a}$ is a $C_6$ aryl group, a —($C_1$-$C_4$ alkylidene)-$C_6$ aryl group or, a $C_6$ aryl group or a —($C_1$-$C_4$ alkylidene)-$C_6$ aryl group, optionally substituted with one, two, three, four, or five $R^4$; wherein $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In some technical solutions, $R^{2a}$ is a phenyl group, a —($C_1$-$C_4$ alkylidene)-phenyl group or, a phenyl group or a —($C_1$-$C_4$ alkylidene)-phenyl group, optionally substituted with one, two, three, four, or five $R^4$; wherein $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In some technical solutions, $R^1$ is H; $R^2$ is $R^{2a}C(=O)$; $R^{2a}$ is a phenyl group, or a phenyl group substituted with $R^4$; $R^4$ is —OH, —$NH_2$, —$NO_2$, —CN, —SH, —$X_2$, a —$C_1$-$C_5$ alkoxy group, or a —$C_1$-$C_5$ alkyl group, wherein $X_2$ is selected from F, Cl, Br, or I; $R^{2b}$ is a $C_1$-$C_{15}$ alkyl group; Y is —OH or —$OC_1$-$C_5$ (an alkoxy group having 1 to 5 carbon atoms); X is —$NHC_1$-$C_5$ (an alkylamino group having one $C_1$-$C_5$ alkyl group).

In some technical solutions, $R^1$ is $R^{1b}C(=O)$ or H; $R^2$ is $R^{2b}C(=O)$; each of $R^{1b}$ and $R^{2b}$ is independently a $C_1$-$C_{20}$ alkyl group, a $C_3$-$C_6$ cycloalkyl group or, a $C_1$-$C_{20}$ alkyl group or a $C_3$-$C_7$ cycloalkyl group optionally substituted with one, two, three, four, or five $R^3$; wherein $R^3$ is —OH, —$NH_2$, —CN, —SH, or —$X_1$, wherein $X_1$ is selected from F, Cl, Br, or I.

In some technical solutions, $R^1$ is or H; $R^2$ is $R^{2b}C(=O)$; $R^{2b}$ is a $C_1$-$C_{20}$ alkyl group, or a $C_1$-$C_{20}$ alkyl group optionally substituted with one, two, three, four, or five $R^3$; $R^3$ is —OH, —$NH_2$, —CN, —SH, or —$X_1$, wherein $X_1$ is selected from F, Cl, Br, or I.

In some technical solutions, Y is an $OC_1$-$C_{10}$ alkyl group.

In some technical solutions, X is a nitrogen-containing $C_4$-$C_{10}$ cycloalkyl group.

In some technical solutions, X is a $NHC_1$-$C_{20}$ alkyl group.

In some technical solutions, X is preferably a $NHC_1$-$C_{10}$ alkyl group.

In another aspect, the present invention provides the use of the above-mentioned glutamine derivative, the racemate thereof, the stereoisomer thereof, the geometric isomer thereof, the tautomer thereof, the solvate thereof, or the feed acceptable salt thereof, in preparing an animal feed additive.

In another aspect, the present invention provides a feed composition, which comprises at least one of the herein provided glutamine derivative, the racemate thereof, the stereoisomer thereof, the geometric isomer thereof, the tautomer thereof, the solvate thereof, and the feed acceptable salt thereof, and an adjuvant suitable for feed, wherein the adjuvant is selected from a carrier, a diluent, an excipient, a dissolvent, or a combination thereof.

In some technical solutions, the feed composition further comprises an animal feed raw material.

In some technical solutions, the feed composition further comprises an additional animal feed additive.

In some technical solutions, the feed composition further comprises an animal feed ingredient and an additional animal feed additive.

In some technical solutions, the additional animal feed additive is selected from a nutritive feed additive and/or a general feed additive and/or a medicinal feed additive.

In another aspect, the present invention provides the use of the feed composition in preparing an animal feed additive.

In another aspect, the present invention provides the use of the feed composition in preparing an animal feed.

In another aspect, the present invention further provides a method for improving the production performance of farmed animals.

Beneficial Effects of the Present Invention

Animal breeding experiments revealed that, the described compounds, including the glutamine derivative, the racemate thereof, the stereoisomer thereof, the geometric isomer thereof, the tautomer thereof, the solvate thereof, and the feed acceptable salt thereof, can be used as animal feed additives and has excellent effect in improving animal production performance such as growth and feed efficiency.

Any embodiment of any aspect of the present invention can be combined with other embodiments as long as there is no contradiction therebetween. Moreover, any technical feature in any embodiment of any aspect of the present invention, can be applied as the same technical feature in other embodiments, as long as there is no contradiction therebetween.

The foregoing content only outlines certain aspects of the present invention, which is however not limited to these aspects. The content involved above and in other aspects will be described in more detail and complete as below.

A further detailed description of the present invention is given below.

Herein certain embodiments of the present invention will be described in detail, examples of which are illustrated by the accompanying structural formulas and chemical formulas. The intention of the present invention covers all substituted, modified, and equivalent technical solutions, which all fall within in the scope of the present invention as defined by the claims. In addition, certain technical features of the present invention, in order to be clearly present, may be described separately in multiple independent embodiments; however, they can also be provided in a single embodiment in combination or in any suitable sub-combination.

Compound

The compound involved in the present invention is a glutamine derivative having a structure of formula (I).

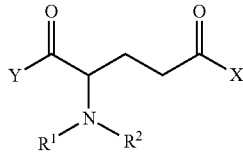

Formula (I)

Wherein, Y is a substituent at the oxygen atom (abbreviated as O) where the active hydrogen atom in the carboxyl group of the glutamine derivative has been substituted. X is a group that is the result of substituting of the amide group of the glutamine derivative on the amino nitrogen atom (abbreviated as N). $R^1$ and $R^2$ are substituents of the amino at nitrogen atom (abbreviated as N).

Furthermore, Y is an $OC_1$-$C_{20}$ alkyl group or OH; X is a nitrogen-containing $C_4$-$C_{10}$ cycloalkyl group, a $NHC_1$-$C_{20}$ alkyl group, or a $N(C_1$-$C_{20}$ alkyl group$)_2$; $R^1$ is $R^{1a}C(=O)$, $R^{1b}C(=O)$, $R^{1a}S(=O)_2$, $R^{1b}S(=O)_2$ or H; $R^2$ is $R^{2a}C(=O)$, $R^{2b}C(=O)$, $R^{2a}S(=O)_2$, or $R^{2b}S(=O)_2$.

Each of $R^{1b}$ and $R^{2b}$ is independently a $C_1$-$C_{20}$ alkyl group or a $C_3$-$C_7$ cycloalkyl group, substituted or unsubstituted; when $R^{1b}$ and/or $R^{2b}$ is a, substituted, $C_1$-$C_{20}$ alkyl group or $C_3$-$C_7$ cycloalkyl group, the $C_1$-$C_{20}$ alkyl group or $C_3$-$C_7$ cycloalkyl group is a $C_1$-$C_{20}$ alkyl group or $C_3$-$C_7$ cycloalkyl group optionally substituted with one, two, three, four, or five $R^3$; $R^3$ is —OH, —$NH_2$, —CN, —SH, or —$X_1$, wherein $X_1$ is selected from F, Cl, Br, or I.

Each of $R^{1a}$ and $R^{2a}$ is independently a $C_5$-$C_{12}$ aryl group, a $C_5$-$C_{12}$ heteroaryl group, a —($C_1$-$C_4$ alkylidene)-$C_5$-$C_{12}$ aryl group, or a —($C_1$-$C_4$ alkylidene)-$C_5$-$C_{12}$ heteroaryl group, substituted or unsubstituted; when $R^{1a}$ or $R^{2a}$ is a, substituted, $C_5$-$C_{12}$ aryl group, $C_5$-$C_{12}$ heteroaryl group, —($C_1$-$C_4$ alkylidene)-$C_5$-$C_{12}$ aryl group or —($C_1$-$C_4$ alkylidene)-$C_5$-$C_{12}$ heteroaryl group, the $C_5$-$C_{12}$ aryl group, $C_5$-$C_{12}$ heteroaryl group, —($C_1$-$C_4$ alkylidene)-$C_5$-$C_{12}$ aryl group, or —($C_1$-$C_4$ alkylidene)-$C_5$-$C_{12}$ heteroaryl group is a $C_5$-$C_{12}$ aryl group, $C_5$-$C_{12}$ heteroaryl group, —($C_1$-$C_4$ alkylidene)-$C_5$-$C_{12}$ aryl group or —($C_1$-$C_4$ alkylidene)-$C_5$-$C_{12}$ heteroaryl group, optionally substituted with one, two, three, four, or five $R^4$; $R^4$ is —OH, —$NH_2$, —$NO_2$, —CN, —SH, —$X_2$, a —$C_1$-$C_5$ alkoxy group, a —$C_1$-$C_5$ alkyl group or a —$C_1$-$C_5$ alkyl group substituted with $X_2$, wherein $X_2$ is selected from F, Cl, Br, or I.

Generally, the term "substituted" indicates that one or more replaceable hydrogen atoms in the given structure have been substituted by specific substituents, wherein one substituted group may have one substituent at each substitutable position of the group, and when more than one position in the given structural formula can be substituted by one or more specific substituents, then the substituents can be substituted at the positions, identically or differently.

In the present invention, a "$OC_a$—$C_b$ alkyl group" is a linear or branched, saturated alkoxy group containing a to b carbon atoms, such as methoxy, ethoxy, propoxy, isopropoxy, . . . ; for example, a "$OC_1$-$C_{10}$ alkyl group" represents a linear or branched, saturated alkoxy group containing 1 to 10 carbon atoms. A "$C_3$-$C_7$ cycloalkyl group" is a cyclic alkyl group containing 3-7 carbon atoms and containing only carbon and hydrogen elements, such as cyclopropyl, 2-methylcyclopropyl, and cyclopentyl. A "$C_1$-$C_5$ alkoxy group" represents a group containing 1 to 5 carbon atoms and one oxygen atom, such as methoxy, ethoxy, propoxy, and isopropoxy. A "$C_5$-$C_{12}$ aryl group" is a cyclic and aromatic group containing 5 to 12 carbon atoms, such as phenyl. A "$C_5$-$C_{12}$ heteroaryl group" is an aromatic and cyclic group containing 5 to 12 carbon atoms and more than one heteroatom (including but not limited to oxygen atom (O), sulfur atom (S), nitrogen atom (N)), such as a pyrrolyl group or a pyridyl group. A "nitrogen-containing $C_n$-$C_m$ cycloalkyl group" is a substituted or unsubstituted cycloalkyl group containing n to m carbon atoms and 1 nitrogen atom, such as a tetrahydropyrrolyl group or a piperidinyl group. A "$NHC_1$-$C_{20}$ alkyl group" is a secondary amino group substituted with a linear or branched saturated alkyl group containing 1 to 20 carbon atoms, such as $NHCH_3$ and $NHCH_2CH_3$.

In some technical solutions, X in the glutamine derivative of formula (I) is a nitrogen-containing $C_4$-$C_{10}$ cycloalkyl group.

Further, X preferably is a tetrahydropyrrolidine group or a piperidinyl group, substituted or unsubstituted.

Much further, when X is a substituted tetrahydropyrrolidine group or a piperidinyl group, it is a tetrahydropyrrolidine group or a piperidinyl group substituted with 1 to 5 linear or branched $C_1$-$C_6$ alkyl groups.

In some embodiments, X in the glutamine derivative of formula (I) is

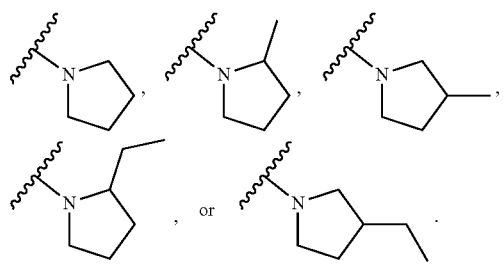

In some other embodiments, X in the glutamine derivative of formula (I) is

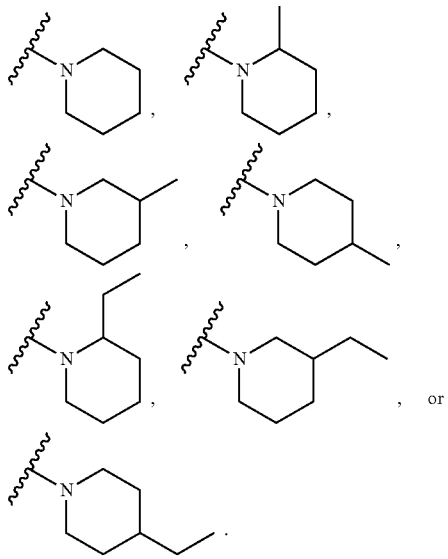

In some embodiments, X in the glutamine derivative of formula (I) is a $NHC_1$-$C_{20}$ alkyl group.

Further, when X is a $NHC_1$-$C_{20}$ alkyl group, the alkyl group is a liner alkyl group.

Much further, X is preferably a $NHC_1$-$C_{10}$ alkyl group, wherein the alkyl group is a liner alkyl group.

In some embodiments, X is $NHCH_3$, $NHCH_2CH_3$, $NH(CH_2)_2CH_3$, $NH(CH_2)_3CH_3$, $NH(CH_2)_4CH_3$, $NH(CH_2)_5CH_3$, $NH(CH_2)_6CH_3$, $NH(CH_2)_7CH_3$, $NH(CH_2)_8CH_3$, or $NH(CH_2)_9CH_3$.

In addition, when X is a $NHC_1$-$C_{20}$ alkyl group, the alkyl group is a branched alkyl group.

Further, when X is preferably a $NHC_1$-$C_{10}$ alkyl group, the alkyl group is a branched alkyl group.

In some embodiments, X includes but is not limited to $NHCH(CH_3)_2$ and $NHC(CH_3)_3$.

In some embodiments, X in the glutamine derivative of formula (I) is a $N(C_1$-$C_{20}$ alkyl group$)_2$.

Further, the alkyl group is preferably a liner alkyl group.

Much further, when the alkyl group is preferably a liner alkyl group, X is preferably a $N(C_1$-$C_{10}$ alkyl group$)_2$.

In some embodiments, X includes but is not limited to a dimethylamino group, a diethylamino group, a di-n-propylamino group, a di-n-butylamino group, a di-n-pentylamino group, a di-n-hexylamino group, a di-n-heptylamino group, a di-n-octylamino group, a di-n-nonylamino group, or a di-n-decylamino group.

In some other embodiments, X in the glutamine derivative of formula (I) is a $N(C_1$-$C_{20}$ alkyl group$)_2$, wherein the alkyl group is a branched alkyl group.

Further, X is preferably a $N(C_1$-$C_{10}$ alkyl group$)_2$, wherein the alkyl group is a branched alkyl group.

In some embodiments, Y in the glutamine derivative of formula (I) is OH.

In some other embodiments, Y in the glutamine derivative of formula (I) is an $OC_1$-$C_{20}$ alkyl group.

Further, the alkyl group is a liner alkyl group.

In some embodiments, Y is selected from $OCH_3$, $OCH_2CH_3$, $O(CH_2)_2CH_3$, $O(CH_2)_3CH_3$, $O(CH_2)_4CH_3$, $O(CH_2)_5CH_3$, $O(CH_2)_6CH_3$, $O(CH_2)_7CH_3$, $O(CH_2)_8CH_3$, and $O(CH_2)_9CH_3$.

In addition, when Y is an $OC_1$-$C_{20}$ alkyl group, the alkyl group is a branched alkyl group.

Further, when Y is preferably an $OC_1$-$C_{10}$ alkyl group, the alkyl group is a branched alkyl group.

In some embodiments, Y includes but is not limited to $OCH(CH_3)_2$ and $OC(CH_3)_3$.

In some embodiments, in the glutamine derivative of formula (I), $R^1$ is $R^{1a}S(=O)_2$ or H, and $R^2$ is $R^{2a}S(=O)_2$.

Further, $R^1$ is preferably H.

In some embodiments, in the glutamine derivative of formula (I), $R^1$ is $R^{1b}S(=O)_2$ or H, and $R^2$ is $R^{2b}S(=O)_2$.

Further, $R^1$ is preferably H.

In some embodiments, in the glutamine derivative of formula (I), $R^1$ is $R^{1a}C(=O)$ or H, and $R^2$ is $R^{2a}C(=O)$.

Further, $R^1$ is preferably H.

In some embodiments, in the glutamine derivative of formula (I), $R^1$ is $R^{1b}C(=O)$ or H, and $R^2$ is $R^{2b}C(=O)$.

Further, $R^1$ is preferably H.

In some embodiments, in the glutamine derivative of formula (I), each of $R^{1a}$ and/or $R^{2a}$ is a substituted or unsubstituted $C_5$-$C_{12}$ aryl group.

Further, the unsubstituted $C_5$-$C_{12}$ aryl group includes but is not limited to a cyclopentadienyl group, a phenyl group or a naphthyl group.

In some embodiments, $R^{1a}$ and/or $R^{2a}$ are

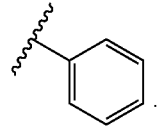

In addition, when $R^{1a}$ and/or $R^{2a}$ are a substituted $C_5$-$C_{12}$ aryl group, the $C_5$-$C_{12}$ aryl group is a $C_5$-$C_{12}$ aryl group optionally substituted with one, two, three, four, or five $R^4$; wherein $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

Further, the $C_5$-$C_{12}$ aryl group is preferably a $C_6$ aryl group.

Specifically, $R^{1a}$ and/or $R^{2a}$ are a substituted phenyl group, which is optionally substituted with one, two, three, four, or five $R^4$; wherein $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In some embodiments $R^{1a}$ and/or $R^{2a}$ are

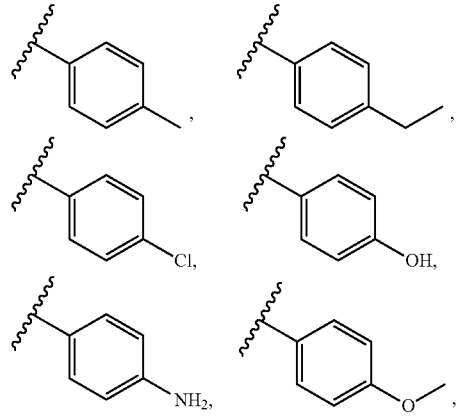

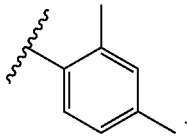

In some embodiments, in the glutamine derivative of formula (I), $R^{1a}$ and/or $R^{2a}$ are a substituted or unsubstituted —($C_1$-$C_4$ alkylidene)-$C_5$-$C_{12}$ aryl group.

Further, when $R^{1a}$ and/or $R^{2a}$ are an unsubstituted —($C_1$-$C_4$ alkylidene)-$C_5$-$C_{12}$ aryl group, the $C_5$-$C_{12}$ aryl group includes but is not limited to a cyclopentadienyl group, a phenyl group or a naphthyl group, and the alkylidene is preferably a methylene group.

In some embodiments, $R^{1a}$ and/or $R^{2a}$ are

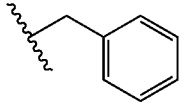 [SMILES: *Cc1ccccc1]

(a benzyl group).

In addition, when $R^{1a}$ and/or $R^{2a}$ are a substituted —($C_1$-$C_4$ alkylidene)-$C_5$-$C_{12}$ aryl group, the $C_5$-$C_{12}$ aryl group is a $C_5$-$C_{12}$ aryl group optionally substituted with one, two, three, four, or five $R^4$; $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

Further, the $C_5$-$C_{12}$ aryl group is preferably a $C_6$ aryl group.

Specifically, $R^{1a}$ and/or $R^{2a}$ are a substituted benzyl group, which is optionally substituted with one, two, three, four, or five $R^4$; $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

In some embodiments, $R^{1a}$ and/or $R^{2a}$ are

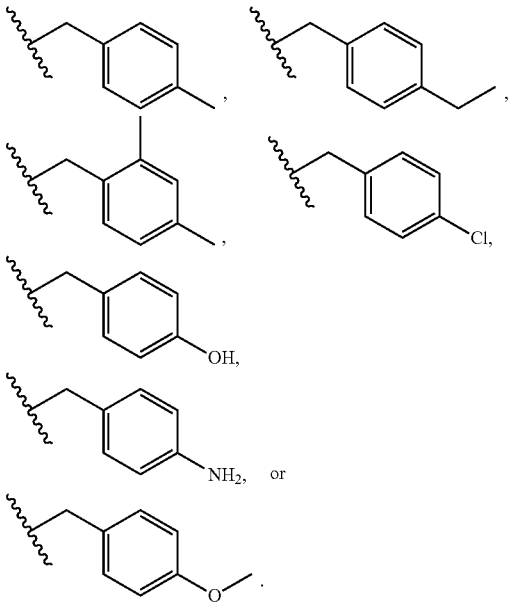

In some embodiments, in the glutamine derivative of formula (I), $R^{1a}$ and/or $R^{2a}$ are a substituted or unsubstituted $C_5$-$C_{12}$ heteroaryl group.

Further, when $R^{1a}$ and/or $R^{2a}$ are an unsubstituted $C_5$-$C_{12}$ heteroaryl group, the $C_5$-$C_{12}$ heteroaryl group includes but is not limited to a pyrrolylalkyl group, a pyrazolyl group, or a pyridyl group.

In some embodiments, $R^{1a}$ and/or $R^{2a}$ are

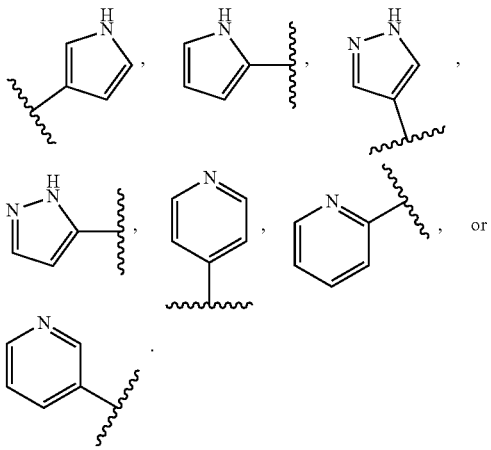

In addition, when $R^{1a}$ and/or $R^{2a}$ are a substituted $C_5$-$C_{12}$ heteroaryl group, the $C_5$-$C_{12}$ heteroaryl group is optionally substituted with one, two, three, four, or five $R^4$; $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

Further, the $C_5$-$C_{12}$ heteroaryl group is preferably a pyrrolyl group, a pyrazolyl group, or a pyridyl group.

In some embodiments, $R^{1a}$ and/or $R^{2a}$ are

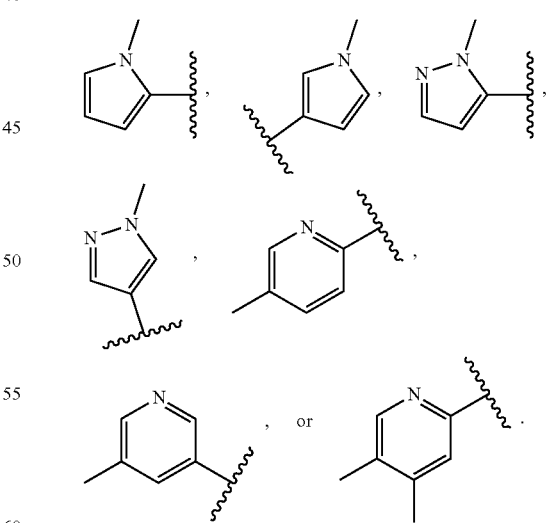

In some embodiments, in the glutamine derivative of formula (I), $R^{1a}$ and/or $R^{2a}$ are a substituted or unsubstituted —($C_1$-$C_4$ alkylidene)-$C_5$-$C_{12}$ heteroaryl group.

Further, the —($C_1$-$C_4$ alkylidene)-$C_5$-$C_{12}$ heteroaryl group is an unsubstituted —($C_1$-$C_4$ alkylidene)-$C_5$-$C_{12}$ heteroaryl group, wherein the $C_5$-$C_{12}$ heteroaryl group includes but is not limited to a pyrrolyl group, a pyrazolyl group, or a pyridyl group, and the $C_1$-$C_4$ alkylidene is preferably a methylene group.

In some embodiments, $R^{1a}$ and/or $R^{2a}$ are

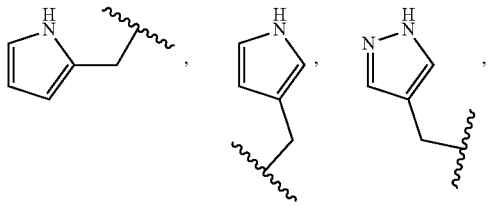

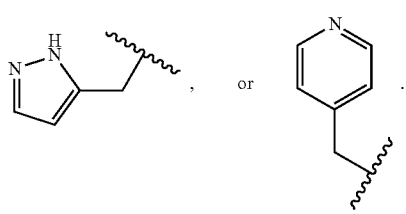

In addition, when $R^{1a}$ and/or $R^{2a}$ are a substituted —($C_1$-$C_4$ alkylidene)-$C_5$-$C_{12}$ heteroaryl group, the $C_5$-$C_{12}$ heteroaryl group is optionally substituted with one, two, three, four, or five $R^4$; $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

Further, the $C_5$-$C_{12}$ heteroaryl group is preferably a pyrrolyl group, a pyrazolyl group, or a pyridyl group, and the $C_1$-$C_4$ alkylidene is preferably a methylene group.

In some embodiments, $R^{1a}$ and/or $R^{2a}$ are

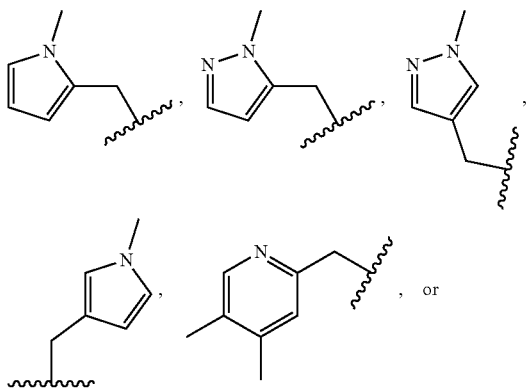

-continued

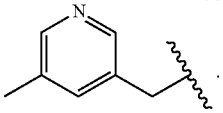

In some embodiments, the glutamine derivative of the present invention includes the above compounds and a racemate thereof, a stereoisomer thereof, a geometric isomer thereof, a tautomer thereof, a solvate thereof, or a feed acceptable salt thereof.

In some embodiments, in the glutamine derivative of formula (I), Y is OH, and the glutamine derivative can further exist in the form of a feed acceptable salt, wherein the feed acceptable salt is a salt of a metal ion.

Further, the metal ion is a monovalent metal ion, a divalent metal ion, or a trivalent metal ion.

Specifically, the monovalent metal ion includes but is not limited to sodium ion, potassium ion, lithium ion, and ammonium ion; the divalent metal ion includes but is not limited to calcium ion, magnesium ion, zinc ion, copper ion, ferrous ion, and manganese ion; the trivalent metal ion includes but is not limited to iron ion, nickel ion, chromium ion, and aluminum ion.

In some embodiments, the metal ion is zinc ion.

In some other embodiments, the metal ion is copper ion.

In some other embodiments, the metal ion is sodium ion.

In some other embodiments, the metal ion is calcium ion.

In some other embodiments, the metal ion is iron ion.

Preparation and Purification of Compounds

The glutamine derivative of formula (I) involved in the present invention is prepared with glutamic acid (abbreviated as Glu) as the starting material. The involved chemical reactions mainly include esterification of carboxyl groups, acylation of amino groups, and aminolysis of esters, and hydrolysis of esters if necessary.

In some embodiments, when Y in the glutamine derivative of formula (I) is OH, the glutamine derivative is prepared by the method as shown in formula (II), wherein the di-tert-butyl glutamate (t-Bu-Glu) can be produced by dehydration condensation between glutamic acid and tert-butanol under esterification conditions:

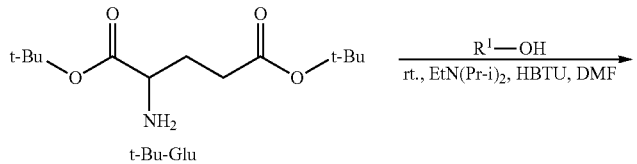

-continued

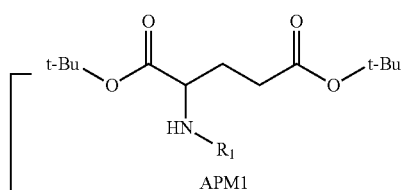
APM1

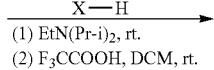
(1) EtN(Pr-i)$_2$, rt.
(2) F$_3$CCOOH, DCM, rt.

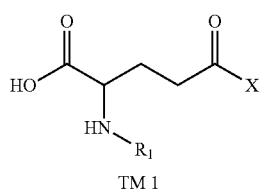
TM 1

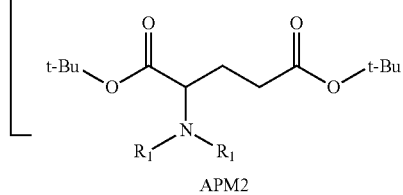
APM2

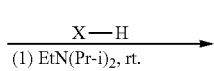
(1) EtN(Pr-i)$_2$, rt.
(2) F$_3$CCOOH, DCM, rt.

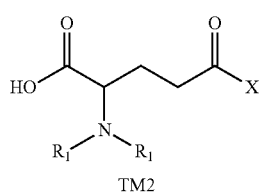
TM2

It should be noted that, X and R$^1$ shown in formula (II) only represent substituent groups; if the stating materials X—H or R$^1$—OH is not a single substance, then X or R$^1$ should be understood as a collection of substituents. The symbol t-Bu is a tert-butyl group as the protecting group of carboxyl group, DCM is dichloromethane, and F$_3$CCOOH is trifluoroacetic acid. Moreover, rt. is room temperature, EtN(Pr-i)$_2$ is diisopropylethylamine, DMF is N,N-dimethylformamide, HBTU is O-(Benzotriazol-1-yl)-N,N,N',N'-tetramethyluronium hexafluorophosphate (a coupling reagent).

Further, when Y in the glutamine derivative of formula (I) is OH, the glutamine derivative may react with a metallic base of a metal of main group I or main group II, or react with a metal halide under alkaline conditions, to obtain a metal ion salt of the glutamine derivative.

Optionally, the metallic base is selected from sodium hydroxide, potassium hydroxide, calcium hydroxide, and magnesium hydroxide.

Optionally, the metal halide is a metal chloride, a metal bromide, or a metal iodide.

Specifically, the metal chloride is zinc chloride, calcium chloride, magnesium chloride, iron chloride, copper chloride, manganese chloride, cobalt chloride, or nickel chloride; the metal bromide is zinc bromide, calcium bromide, magnesium bromide, iron bromide, copper bromide, manganese bromide, cobalt bromide, or nickel bromide; the metal iodide is zinc iodide, calcium iodide, magnesium iodide, iron iodide, copper iodine, manganese iodide, cobalt iodide, or nickel iodide.

In some embodiments, when Y in the glutamine derivative of formula (I) is an OC$_1$-C$_{20}$ alkyl group, the glutamine derivative is prepared by the method as shown in formula (III), wherein the di-tert-butyl glutamate (t-Bu-Glu) can be produced by dehydration condensation between glutamic acid and tert-butanol under esterification conditions:

Formula (III)

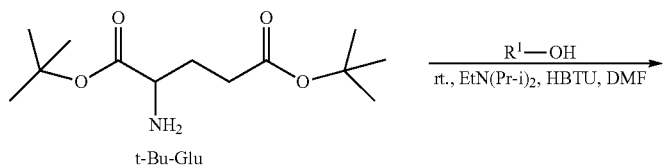
t-Bu-Glu

R$^1$—OH
rt., EtN(Pr-i)$_2$, HBTU, DMF

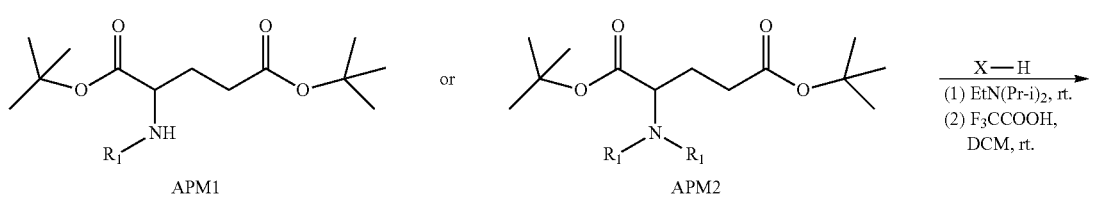
APM1 or APM2

X—H
(1) EtN(Pr-i)$_2$, rt.
(2) F$_3$CCOOH, DCM, rt.

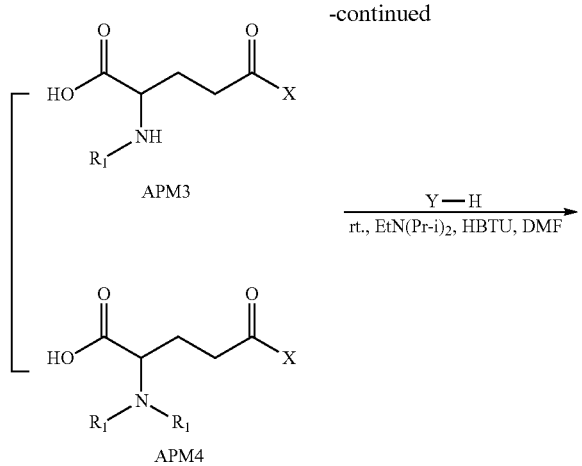

It should be noted that, Y, X and $R^1$ shown in formula (III) only represent substituent groups; if the stating material $R^1$—OH is not a single substance, then $R^1$ should be understood as a collection of substituents. The symbol t-Bu is a tert-butyl group as the protecting group of carboxyl group, DCM is dichloromethane, and $F_3CCOOH$ is trifluoroacetic acid. Moreover, rt. is room temperature, $EtN(Pr-i)_2$ is diisopropylethylamine, DMF is N,N-dimethylformamide, HBTU is O-(Benzotriazol-1-yl)-N,N,N',N'-tetramethyluronium hexafluorophosphate (a coupling reagent).

In some embodiments, the glutamine derivative is a chiral compound, which is prepared from dibutyl glutamate with a chiral structure (as shown in formula (IV)) or its racemate. The glutamine derivative of the present invention may be selected from stereoisomers such as levo L-(−)-glutamine derivative (formula (V)), dextro D-(+)-glutamine derivative (formula (VI)), and racemic DL-(±)-glutamine derivative.

Formula (IV)

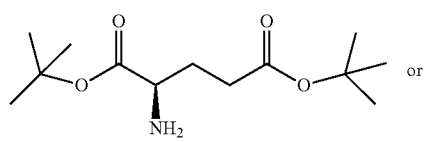

Formula (V)

Formula (VI)

It should be noted that, $R^1$ shown in formula (V) and formula (VI) only represents identical and/or different substituent groups.

In some embodiments, the chiral stereoisomers of the glutamine derivative can undergo transformation of spatial configuration under suitable conditions. For example, a conformational interconversion of glutamine derivative, which results in tautomers, is as shown in formula (VII):

Formula (VII)

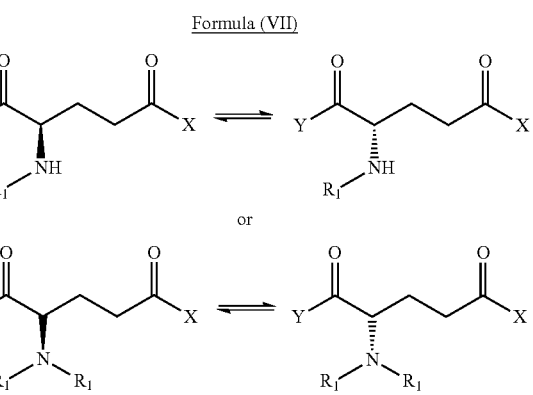

When the reaction of the involved reactants results in the corresponding glutamine derivative having a rigid structure, the reaction may produce different geometric isomers from the reactants.

The aforementioned stereoisomers, geometric isomers, and tautomers are also included in the scope of the present invention.

The term "stereoisomers" refers to compounds with the same chemical structure but different arrangement of their atoms or groups in space, including enantiomers, diastereomers, conformational isomers, geometric isomers, and atropisomers. The term "enantiomers" refers to two isomers that are non-superimposable mirror images of each other. The term "diastereomers" refers to two stereoisomers with two or more chiral centers but are not mirror images of each other; they are different in physical properties such as melting point, boiling point, spectral properties and reactivity. A mixture of diastereomers can be separated by high-resolution analysis such as electrophoresis or chromatography. The term "tautomers" refers to structural isomers with different energies and interchangeable through a low energy barrier.

In some embodiments, the process of preparing the glutamine derivative provided by the present invention also involves the isolation, purification, or recrystallization of the reaction product. The reaction product can be obtained as a crude product from the reaction system by removing the solvent. In order to obtain a solid substance with higher chemical purity and lower impurity level, the crude product can be dissolved, and crystallized or precipitated or recrystallized in alcohol solvents, alcohol-water solvents or other organic solvents that can be used for product recrystallization under suitable temperature, light, and mechanical vibration conditions, and then isolated to obtain the glutamine derivative of a certain crystal state. The glutamine derivative of a certain crystal state refers to a crystal of the glutamine derivative or a solvate of the glutamine derivative. The solvate of the glutamine derivative can be selected from a hydrate of the glutamine derivative or an ethanolate of the glutamine derivative.

The "solvate" involved in the present invention refers to a co-crystal complex formed by the compound of the present invention being combined with chemically equivalent or non-chemically equivalent molecules of a solvent through non-covalent intermolecular forces, caused by external factors and internal factors when contacting the compound with the solvent. Solvents for forming the solvate include but are not limited to water, acetone, ethanol, methanol, dimethyl sulfoxide, ethyl acetate, acetic acid, and isopropanol. The "hydrate" refers to a complex or a crystal where the solvent is water, i.e., the compound being combined with chemically equivalent or non-chemically equivalent water molecules through non-covalent intermolecular forces.

In order to obtain a solid substance with higher chemical purity and lower impurity level, the process of preparing the glutamine derivative provided by the present invention may also involve a salting-out process. The salting-out process refers to a process of forming a salt from the acyl derivative of glutamine with a corresponding organic base, inorganic base, organic acid, or inorganic acid, by acid-base neutralization, acid-base coordination, or acid-base chelation, and thereby precipitating the salt to obtain a feed acceptable salt. The inorganic acid includes, but is not limited to, hydrochloride, hydrobromide, phosphate, sulfate, nitrate, or a combination thereof. The organic base includes, but is not limited to, ammonia or triethylamine. The inorganic base includes, but is not limited to, sodium hydroxide, potassium hydroxide, magnesium hydroxide, or calcium hydroxide.

The feed acceptable salt refers to a salt of the glutamine derivative with an organic base, inorganic base, organic acid or inorganic acid, those are non-toxic to animals. The term "feed acceptable" refers to that the substance or composition must by chemically or toxicologically suitable for and relevant to the resulting feed or fed animals.

In some embodiments, the glutamine derivative of the present invention is an ester glutamine derivative. During the salting-out process, an acid-base coordination salt and/or acid-base chelate salt is formed from the derivative with an inorganic acid or organic acid, wherein the organic acid includes, but is not limited to, acetate, maleate, succinate, mandelate, fumarate, malonate, malate, 2-hydroxypropionate, pyruvate, oxalate, glycolate, salicylate, glucuronate, galacturonate, citrate, tartrate, aspartate, glutamate, benzoate, p-toluene, cinnamate, p-toluenesulfonate, benzenesulfonate, methanesulfonate, ethanesulfonate, triflate, or a combination thereof.

Use of the Glutamine Derivative of the Present Invention

The glutamine derivative, the racemate thereof, the stereoisomer thereof, the geometric isomer thereof, the tautomer thereof, the solvate thereof, or the feed acceptable salt thereof, provided by the present invention, can be used in preparing animal feed additives.

The "animal" involved in the present invention refers to human or farmed animals who cannot synthesize organic substances from inorganic substances, but can only utilize organic substances as food for life activities such as feeding, digestion, absorption, breathing, circulation, excretion, sensation, movement, and reproduction. The "farm animals" include poultry, livestock, aquatic animals, and other artificial fed animals which include pets such as cats and dogs. The term "livestock" comprises, for example, pigs, cattle, horses, goats, sheep, deer, and any species of a variety of useful rodents. The term "poultry" comprises, for example, chickens, ducks, geese, quails, and pigeons. The term "aquatic animals" comprises, for example, fish, shrimps, turtles, and soft-shelled turtles.

The glutamine derivative, the racemate thereof, the stereoisomer thereof, the geometric isomer thereof, the tautomer thereof, the solvate thereof, or the feed acceptable salt thereof, provided by the present invention, can be used in preparing non-nutritive feed additives for improving the production performance of animals at every growth stage, wherein the animals can be selected from livestock, poultry, aquatic animals or pet, at every growth stage.

Further, the livestock includes but is not limited to pigs, cattle, horses, rabbits, sheep, horses, rabbits, martens and donkeys; the poultry includes but is not limited to chickens, turkeys, ducks, geese, quails or pigeons; the aquatic animals include but are not limited to fish, shrimps, turtles, crabs, soft-shelled turtles, bullfrogs, eels and loaches; the pets include but are not limited to dogs or cats of various subspecies.

In one embodiment, the glutamine derivative, the racemate thereof, the stereoisomer thereof, the geometric isomer thereof, the tautomer thereof, the solvate thereof, or the feed acceptable salt thereof, provided by the present invention, is used in preparing feed additives for improving the production performance of hogs, exhibiting improvement effect on the average daily weight gain and feed efficiency.

In another embodiment, the feed additives prepared from the glutamine derivative, the racemate thereof, the stereoisomer thereof, the geometric isomer thereof, the tautomer thereof, the solvate thereof, or the feed acceptable salt thereof, provided by the present invention, can significantly improve the production performance of broilers or layers.

In one embodiment, the glutamine derivative, the racemate thereof, the stereoisomer thereof, the geometric isomer thereof, the tautomer thereof, the solvate thereof, or the feed acceptable salt thereof, provided by the present invention, is used in preparing feed additives for improving the production performance of fish.

The feed acceptable salt of the glutamine derivative, provided by the present invention and used in preparing animal feed additives, is a metal ion salt.

Optionally, the feed acceptable salt of the glutamine derivative is a metal ion salt of the glutamine derivative of formula (I).

Further, Y in the glutamine derivative of formula (I) is OH, and the metal ion salt is a salt that meets the requirements on the preparation of feed additives or feeds, and formed by ion exchange between the OH group and a metal ion when Y in the glutamine derivative of formula (I) is OH.

Specifically, the metal ion is selected from a monovalent metal ion, a divalent metal ion, or a trivalent metal ion.

In some embodiments, the monovalent metal ion is sodium ion (Na(I)), potassium ion (K(I)), or lithium ion (Li(I)).

In some embodiments, the divalent metal ion is calcium ion Ca(II), magnesium ion Mg(II), copper ion Cu(II), zinc ion Zn(II), ferrous ion Fe(II), manganese ion Mn(II), cobalt ion Co(II), or nickel ion Ni(II).

In one embodiment, the metal ion salt of the glutamine derivative used in the preparation of animal feed additives is a zinc ion salt, and the animal feed additives are organic zinc preparations for animals, as a substitute for high level inorganic zinc.

In one embodiment, the metal ion salt of the glutamine derivative used in the preparation of animal feed additives is a copper ion salt, and the animal feed additives are organic copper preparations for animals, as a substitute for high level inorganic copper for animals.

In one embodiment, the metal ion salt of the glutamine derivative used in the preparation of animal feed additives is an iron ion salt, and the animal feed additives are iron supplements for animals In some embodiments, the trivalent metal ion is aluminum ion Al(III), chromium ion Cr(III), or iron ion Fe(III).

Feed Compositions Involved in the Present Invention

A feed composition comprises at least one of the glutamine derivative, the racemate thereof, the stereoisomer thereof, the geometric isomer thereof, the tautomer thereof, the solvate thereof, and the feed acceptable salt thereof, and an adjuvant suitable for feeds. The excipient for feeds can be a carrier, a diluent, an excipient, a dissolvent or a combination thereof.

The feeds involved in the present invention refer to products that are industrially processed and manufactured for animal consumption.

The term "composition" refers to a collection of compounds comprising one or more compounds as active ingredients.

The "comprise," "include," "contain," "with" and variants thereof in the present invention mean an open expression, which includes the contents explicitly stated in the present invention and does not exclude contents of other aspects.

The term "carrier" refers to a substance suitable for feed, which can carry active ingredients, improve their dispersibility, and exhibits high chemical stability and adsorption. The carrier can be an organic carrier or inorganic carrier.

Organic carriers are materials rich in crude fibers, including but not limited to corn flour, corn cob flour, wheat bran, rice husk flour, defatted rice bran, rice bran, corn stalk flour, and peanut husk flour. Inorganic carriers are minerals, mainly classified into calcium salts and silicon oxides and used for the production of trace element premixes, including but not limited to calcium carbonate, silicate, vermiculite, zeolite, and meerschaum.

The term "diluent" refers to a substance that uniformly disperse the additive raw materials, and dilutes the high concentrations of additive raw materials into low-concentration premixed agents or premixes, which separates trace components and reduces interactions between active ingredients, so as to increase the stability of the active ingredients without affecting the physical and chemical properties of involved substances. The diluent can be an organic diluent or inorganic diluent. Organic diluents include but are not limited to corn flour, degerminated corn flour, dextrose (glucose), sucrose, semolina with bran, fried soybean flour, secondary flour, and corn gluten meal. Inorganic diluents include but are not limited to limestone, calcium dihydrogen phosphate, shell powder, kaolin (white clay), table salt and sodium sulfate.

The excipient refers to a wetting agent that induces the inherent viscosity of a substance, an adhesive that binds the substances together, a disintegrant that breaks the entire sheet of a substance into many fine particles, a retention aid that reduces the friction between particles, or an anti-adhesion agent to prevent material adhesion, including but not limited to magnesium stearate, talc, plant oils, magnesium lauryl sulfate, starch, starch slurry, water, inorganic salts, dextrin, and powdered sugar.

The term "dissolvent" refers to a solvent required to dissolve or disperse solids, including but not limited to water, ethanol, and glycerin.

In some embodiments, the feed composition further comprises an additional animal feed additive and/or animal feed raw material.

Animal feed additives include nutritive feed additives, general feed additives, or medicinal feed additives.

The nutritive feed additives refer to substances, in small or trace amounts, that are added to a compound feed for balancing feed nutrients, improving feed utilization, and exhibiting direct nutritional effects on animals, which include amino acids, amino acid salts and their analogs, vitamins and vitamin-like substances, mineral elements and their complexes (chelates), microbial enzyme preparations or non-protein nitrogen.

The general feed additives, also called non-nutritive additives, refer to non-nutritive substances that are added into the feed to improve feed utilization and to ensure feed quality and properties, and are beneficial to animal health or metabolism, including growth promoters, vermifuges, flavorings, attractants, feed conditioners, feed modifiers, feed storage agents and Chinese herbal medicine additives.

Further specifically, the non-nutritive additives are growth promoters, including but not limited to butyric acid, calcium butyrate, sodium butyrate, tannic acid, p-thymol, p-thymol esters, p-thymol salts, 2-hydroxybenzoic acid, β-acids, β-acid esters, β-acid salts, hexahydro β-acids, hexahydro β-acid esters, hexahydro β-acid salts, benzoic acid or calcium benzoate, zinc oxide, zinc sulfate, and zinc chloride.

In one embodiment, the non-nutritive additive is calcium butyrate.

In another embodiment, the non-nutritive additive is tannic acid.

Specifically, medicinal feed additives include but are not limited to premixed veterinary drugs with carrier or diluent, that are capable of preventing animal diseases or promoting animal growth and can be presented in feeds for a long-term use.

Further specifically, the medicinal feed additives are feed antibiotics, and the feed antibiotics include but are not limited to polymyxin, salinomycin, avilamycin, bacitracin, virginiamycin, nasitide, flavomycin, enramycin, kitasamycin, olaquindox, oxytetracycline, or chlortetracycline.

In some embodiments, the compositions comprising the glutamine derivative, the racemate thereof, the stereoisomer thereof, the geometric isomer thereof, the tautomer thereof, the solvate thereof, or the feed acceptable salt thereof, further comprise one or more of nutritive feed additives, general feed additives, and medicinal feed additives.

In some embodiments, the animal feed raw materials are grains and their processed products, oilseeds and their processed products, legumes and their processed products, tubers/tuberous roots and their processed products, other seeds and fruits and their processed products, forages/roughages and their processed products, other plants/algae and their processed products, dairy products and their by-products, terrestrial animal products and their by-products, fish/other aquatic organisms and their by-products, minerals, microbial fermentation products and by-products, other feed raw materials.

Use of Feed Compositions

The present invention involves the use of the above feed compositions comprising the glutamine derivative, the racemate thereof, the stereoisomer thereof, the geometric isomer thereof, the tautomer thereof, the solvate thereof, or the feed acceptable salt thereof.

In some embodiments, the feed compositions comprising the glutamine derivative, the racemate thereof, the stereoisomer thereof, the geometric isomer thereof, the tautomer thereof, the solvate thereof, or the feed acceptable salt thereof, can be used in preparing animal feed additives.

The animal feed additives, prepared from the feed compositions comprising the glutamine derivative, the racemate thereof, the stereoisomer thereof, the geometric isomer thereof, the tautomer thereof, the solvate thereof, or the feed acceptable salt thereof, are livestock feed additives, poultry feed additives, aquatic animal feed additives, or pet feed additives.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feed additives for livestock, wherein the livestock include but are not limited to pigs, cattle, sheep, horses, rabbits, and minks, of various growth stages.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feed additives for poultry, wherein the poultry include but are not limited to chickens, ducks, geese, and pigeons, of various growth stages.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feed additives for aquatic animals, wherein the aquatic animals include but are not limited to fish, shrimps, crabs, soft-shelled turtles, and eels, of various growth stages.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feed additives for pets, wherein the pets include but are not limited to farm-raised dogs or cats.

In some embodiments, the animal feed additives, prepared from the feed compositions comprising the glutamine derivative, the racemate thereof, the stereoisomer thereof, the geometric isomer thereof, the tautomer thereof, the solvate thereof, or the feed acceptable salt thereof, are premixes, multi-premixes, aqueous solutions, or granules.

In some embodiments, the feed compositions comprising the glutamine derivative, the racemate thereof, the stereoisomer thereof, the geometric isomer thereof, the tautomer thereof, the solvate thereof, or the feed acceptable salt thereof, are used in preparing animal feeds.

The animal feeds, prepared from the feed compositions comprising the glutamine derivative, the racemate thereof, the stereoisomer thereof, the geometric isomer thereof, the tautomer thereof, the solvate thereof, or the feed acceptable salt thereof, are livestock feeds, poultry feeds, aquatic animal feeds, or pet feeds.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feeds for livestock, wherein the livestock include but are not limited to pigs, cattle, sheep, horses, rabbits, and minks, of various growth stages.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feeds for poultry, wherein the poultry include but are not limited to chickens, ducks, geese, and pigeons, of various growth stages.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feeds for aquatic animals, wherein the aquatic animals include but are not limited to fish, shrimps, crabs, soft-shelled turtles, and eels, of various growth stages.

Specifically, the feed compositions comprising the glutamine derivative, the racemate thereof, the stereoisomer thereof, the geometric isomer thereof, the tautomer thereof, the solvate thereof, or the feed acceptable salt thereof, are used to prepare feeds for pets, wherein the pets include but are not limited to farm-raised dogs or cats.

In some embodiments, the animal feeds, prepared from the feed compositions comprising the glutamine derivative, the racemate thereof, the stereoisomer thereof, the geometric isomer thereof, the tautomer thereof, the solvate thereof, or the feed acceptable salt thereof, are single feeds, concentrated feeds, formula feeds, multi-premixes or concentrate supplements.

Specifically, the compound feeds are complete compound feeds.

Methods for Improving Production Performance of Farmed Animals

In some feeding embodiments, production performance of animals can be significantly improved by farmers giving feeds in combination with the feed additives comprising the glutamine derivative, the racemate thereof, the stereoisomer thereof, the geometric isomer thereof, the tautomer thereof, the solvate thereof, or the feed acceptable salt thereof, to the animals.

In some embodiments, the feed additives are premixes, multi-premixes, granules, or aqueous solutions, and provided to animals after mixed with animal feeds.

The animals are livestock, poultry, aquatic animals, or pets.

Specifically, the livestock include but are not limited to pigs, cattle, sheep, horses, rabbits, and minks, of various growth stages; the poultry include but are not limited to chickens, ducks, geese, and pigeons, of various growth stages; the aquatic animals include but are not limited to fish, shrimps, crabs, soft-shelled turtles, and eels, of various growth stages; the pets include but are not limited to farm-raised dogs or cats.

In one embodiment, farmers give the feeds in combination with the feed additives comprising the glutamine derivative, the racemate thereof, the stereoisomer thereof, the geometric isomer thereof, the tautomer thereof, the solvate thereof, or the feed acceptable salt thereof, to weaned pigs, which significantly improves the average daily weight gain and feed efficiency of the weaned pigs.

In one embodiment, farmers give the feeds in combination with the feed additives comprising the glutamine derivative, the racemate thereof, the stereoisomer thereof, the geometric isomer thereof, the tautomer thereof, the solvate thereof, or the feed acceptable salt thereof, to broilers, which significantly reduces the feed conversion ratio and improves the feed efficiency of the broilers.

In one embodiment, farmers give the feeds in combination with the feed additives comprising the glutamine derivative, the racemate thereof, the stereoisomer thereof, the geometric isomer thereof, the tautomer thereof, the solvate thereof, or the feed acceptable salt thereof, to fish.

In one embodiment, farmers give the feeds in combination with the feed additives comprising the glutamine derivative, the racemate thereof, the stereoisomer thereof, the geometric isomer thereof, the tautomer thereof, the solvate thereof, or the feed acceptable salt thereof, to young dogs.

In some other feeding embodiments, production performance of animals can be significantly improved by farmers giving the feed compositions comprising the glutamine derivative, the racemate thereof, the stereoisomer thereof, the geometric isomer thereof, the tautomer thereof, the solvate thereof, or the feed acceptable salt thereof, to the animals.

Optionally, the feed compositions are feed additive premixes, feed additive multi-premixes, granules, or aqueous solutions, given in combination with feeds to the animals.

In one embodiment, the feed compositions are feed additive premixes.

In one embodiment, the feed compositions are feed additive compound multi-premixes.

Optionally, the feed compositions are concentrated feeds, compound feeds, formula premixes or concentrate supplements, which are directly given to animals as animal feeds In one embodiment, the feed compositions are complete formula feeds.

DETAILED DESCRIPTION OF THE EMBODIMENTS

The embodiments of the present invention will be described in detail below with examples, but those skilled in the art will understand that the following examples are only used to illustrate the present invention and should not be regarded as limiting the scope of the present invention. If specific conditions are not indicated in the examples, they shall be carried out in accordance with the conventional conditions or the conditions recommended by the manufacturer. Where the involved reagents or instruments are presented without manufactures' names, they are all conventional products that can be commercially purchased.

Breeding Experiments

Glutamine derivatives involved in the breeding experiments are as shown in Table 1.

TABLE 1

Glutamine derivative

| Serial number | R¹ | R² | Y | X |
| --- | --- | --- | --- | --- |
| Compound 1 | H | benzoyl (PhC(O)–) | HO– | –NHEt |
| Compound 2 | H | benzoyl (PhC(O)–) | HO– | –NHBu |

TABLE 1-continued

Glutamine derivative

| Serial number | R¹ | R² | Y | X |
|---|---|---|---|---|
| Compound 3 | H | benzoyl (PhC(O)-) | HO- | -NH-(CH₂)₈-CH₃ |
| Compound 4 | H | benzoyl (PhC(O)-) | HO- | -NH-(CH₂)₁₀-CH₃ |
| Compound 5 | H | benzoyl (PhC(O)-) | HO- | piperidin-1-yl |
| Compound 6 | H | benzoyl (PhC(O)-) | -O-ethyl | -NH-ethyl |
| Compound 7 | H | benzoyl (PhC(O)-) | -O⁻ · Zn²⁺ | -NH-ethyl |
| Compound 8 | H | benzoyl (PhC(O)-) | -O⁻ · Cu²⁺ | -NH-ethyl |
| Compound 9 | H | benzoyl (PhC(O)-) | -O⁻ · Ca²⁺ | -NH-ethyl |
| Compound 10 | H | 4-chlorobenzoyl (4-Cl-C₆H₄-C(O)-) | HO- | -NH-ethyl |

TABLE 1-continued

Glutamine derivative

| Serial number | R¹ | R² | Y | X |
|---|---|---|---|---|
| Compound 11 | H | 4-methylbenzoyl | HO– | –NHEt |
| Compound 12 | H | 4-hydroxybenzoyl | HO– | –NHEt |
| Compound 13 | H | –C(O)(CH₂)₂CH₃ (propanoyl, n=2) | HO– | –NHEt |
| Compound 14 | H | –C(O)(CH₂)₈CH₃ (n=8) | HO– | –NHEt |
| Compound 15 | H | –C(O)(CH₂)₁₂CH₃ (n=12) | HO– | –NHEt |

Note:
It should be clarified that, the Y groups in compounds 8 to 10 only represents the combination of substances, but does not show the salt structures represented by the compounds.

Example 1: Effect of the Glutamine Derivatives on the Production Performance of Hogs 480 65-day-old Duroc×Landrace×Yorkshire cross-bred bacon-type pigs with similar body weight, were randomly divided into 16 groups, with 3 replications per group and 10 pigs (half of male and female) per replication. The pig pen and tools were sterilized before the experiment. During the experiment, the piglets were kept in separate regions in the same pig pen under the same feeding and management conditions. The piglets were given ad libitum access to food and water, and feeds were provided twice every day. The groups comprised one control group and treatment groups 2 to 16, wherein piglets of the control group were given basal ration only, while piglets of the treatment groups 2 to 16 were respectively given basal ration in combination with 800 ppm of different glutamine derivatives, as shown in Table 2. During the entire process, each treatment group was not given other antioxidants or growth promoters. The experiment lasted for 28 days. At the day when the piglets were 93-day old and without withdrawing feed and water for 12 hours, taking each replicate as one unit, body weights of the piglets were measured for calculating average daily feed intake (ADFI, g/d per piglet), average daily weigh gain (ADG, g/d per piglet), and feed conversion ratio (FCR).

Average daily feed intake=(Total weight of provided feed−Weight of remaining feed)/(Number of days×Amount of piglets in each replicate)

Average daily weight gain=(Average final body weight−Average initial body weight)/Number of days Feed conversion ratio=Average daily feed intake/ Average daily weight gain Results were as shown in Table 2, wherein the effect of the samples on the production performance of piglets was evaluated in terms of three aspects: feed intake, weight gain, and feed efficiency.

TABLE 2

Effect of the glutamine derivatives on the production performance of piglets

| Group | Sample | ADFI (g/d per piglet) | ADG (g/d per piglet) | FCR |
|---|---|---|---|---|
| 1 | — | 1586 | 588 | 2.695 |
| 2 | Compound 1 | 1657 | 661 | 2.506 |
| 3 | Compound 2 | 1648 | 651 | 2.531 |
| 4 | Compound 3 | 1691 | 670 | 2.524 |
| 5 | Compound 4 | 1602 | 641 | 2.500 |
| 6 | Compound 5 | 1633 | 651 | 2.510 |
| 7 | Compound 6 | 1615 | 646 | 2.499 |
| 8 | Compound 7 | 1674 | 672 | 2.491 |
| 9 | Compound 8 | 1670 | 671 | 2.488 |
| 10 | Compound 9 | 1636 | 652 | 2.511 |
| 11 | Compound 10 | 1607 | 657 | 2.508 |
| 12 | Compound 11 | 1592 | 634 | 2.512 |
| 13 | Compound 12 | 1599 | 633 | 2.528 |
| 14 | Compound 13 | 1609 | 627 | 2.566 |
| 15 | Compound 14 | 1582 | 621 | 2.548 |
| 16 | Compound 15 | 1670 | 650 | 2.571 |

As can be seen from the results, the samples had no significant effect on the feed intake of the piglets, even though increase in feed intake was observed in several treatment groups as compared with the control group. However, the average daily weight gain of every treatment group had increased to varying degrees regardless of change in feed intake. In terms of feed conversion ratio, a reduction of 4.6%-7.6% was observed in every treatment group as compared with the control group, wherein the treatment groups 8 to 10 exhibited the most significant results.

Example 2: Effect of the Glutamine Derivatives on the Production Performance of Broilers The experiment was conducted with single-factor randomized design. 720 1-day-old yellow broilers with a similar average body weight of 50 g, was randomly divided into 16 groups, each group consisting of 3 replicates and equal numbers of males and females, and each replicate consisting of 15 yellow broilers. The chicken house and tools were sterilized before the experiment. During the experiment, the broilers were kept in separate regions in the same chicken house under the same feeding and management conditions. Basal ration mainly consisted of corn and soybean meal. During the entire process, each treatment group was not given other antioxidants or growth promoters. The groups comprised one control group and treatment groups 2 to 16, wherein broilers of the control group were given basal ration only, while broilers of the treatment groups 2 to 16 were respectively given basal ration in combination with 750 ppm of different glutamine derivatives, as shown in Table 3. The experiment lasted for 20 days. The broilers were given ad libitum access to food and water, and feeds were provided twice every day. At the day when the broilers were 21-day old (withdrawing feed for 12 hours, without withdrawing water), taking each replicate as one unit, body weights of the broilers were measured for calculating average daily feed intake (ADFI, g/d per broiler), average daily weigh gain (ADG, g/d per broiler), and feed conversion ratio (FCR).

Feed conversion ratio (FCR)=Average daily feed intake/Average daily weight gain

TABLE 3

Effect of the glutamine derivatives on the production performance of broilers

| | Sample | ADFI (g/d per broiler) | ADG (g/d per broiler) | FCR |
|---|---|---|---|---|
| 1 | — | 31.1 | 12.6 | 2.47 |
| 2 | Compound 1 | 32.8 | 14.8 | 2.22 |
| 3 | Compound 2 | 31.5 | 14.1 | 2.23 |
| 4 | Compound 3 | 31.9 | 14.4 | 2.21 |
| 5 | Compound 4 | 32.1 | 14.3 | 2.25 |
| 6 | Compound 5 | 30.9 | 13.7 | 2.26 |
| 7 | Compound 6 | 31.2 | 14.2 | 2.20 |
| 8 | Compound 7 | 31.7 | 14.5 | 2.18 |
| 9 | Compound 8 | 30.6 | 14.2 | 2.16 |
| 10 | Compound 9 | 32.5 | 14.8 | 2.20 |
| 11 | Compound 10 | 32.2 | 14.5 | 2.22 |
| 12 | Compound 11 | 30.8 | 13.8 | 2.24 |
| 13 | Compound 12 | 31.6 | 14.0 | 2.26 |
| 14 | Compound 13 | 31.3 | 13.7 | 2.28 |
| 15 | Compound 14 | 31.8 | 14.0 | 2.27 |
| 16 | Compound 15 | 32.4 | 14.6 | 2.22 |

Results were as shown in Table 3. As can be seen from the results, the samples had no significant effect on the feed intake of the broilers. In terms of average daily weight gain, the treatment groups exhibited a significant increase of 8.7%-17.4% as compared with the control group. The samples exhibited a significantly improvement effect on the feed conversion ratio of each treatment group, giving a reduction of 7.6%-10.9%. Among others, the treatment groups 8-10, which are given the zinc salt, copper salt, and calcium salt of N-benzoyltheanine, exhibited a reduction of 10.9%-12.5% as compared with the control group.

Example 3: Application of the Glutamine Derivatives in Fish Feed

Grass carps were used in this experiment, which is conducted in an aquaculture region in the Guangzhou Insighter experiment yard. Healthy grass carps with the same size were reared in large netcages for 4 weeks before the experiment. The grass carps were kept in small floating netcages during the experiment. The small netcages and netcages for acclimatization were both placed in a 3500 m² pond in the experiment yard. The pond had a water depth of 1.5 m, and water therein was aerated from the bottom. In the experiment, 520 grass carps, which had been starved for 1 day, were randomly divided into 13 groups, each group consisting of 4 replicates, and each replicate consisting of 10 grass carps. The grass carps were weighed, taking each replicate as a whole. Then they were randomly released to 52 netcages in which they were fed with different feeds. The feeds used in this experiment were prepared according to Table 4, wherein 500 ppm of different glutamine derivatives was added to the basal rations for different treatment groups. Feed restriction had been adopted during the experiment, and the feeding amount was adjusted once a week. The treatment and control groups were fed twice (7:30 and 15:30) every day, with their feeding levels (based on initial body weights) being identical to be a total amount of 580 g. The experiment lasted for 8 weeks.

Calculation:

Weight gain rate (%)=(Average final weight−Average initial weight)/Average initial weight×100

Feed coefficient=580/(Average final weight−Average initial weight)

Table 4 shows the effect of different glutamine derivatives on the production performance of grass carps, which was evaluated in terms of two aspects, weight gain rate and feed coefficient.

TABLE 4

Grouping and results for evaluating the application of glutamine derivatives in fish feed

| | Sample | Average initial weight (g) | Average final weight (g) | Weight gain rate (%) | Feed coefficient |
|---|---|---|---|---|---|
| 1 | — | 386 | 649 | 68.19 | 1.93 |
| 2 | Compound 1 | 393 | 678 | 72.41 | 1.79 |
| 3 | Compound 2 | 405 | 690 | 70.47 | 1.78 |
| 4 | Compound 3 | 382 | 666 | 74.29 | 1.79 |
| 5 | Compound 4 | 388 | 675 | 73.97 | 1.77 |
| 6 | Compound 5 | 396 | 678 | 71.27 | 1.80 |
| 7 | Compound 6 | 394 | 681 | 72.84 | 1.77 |
| 8 | Compound 10 | 388 | 669 | 72.34 | 1.81 |
| 9 | Compound 11 | 399 | 681 | 70.73 | 1.80 |
| 10 | Compound 12 | 408 | 692 | 69.56 | 1.79 |
| 11 | Compound 13 | 403 | 687 | 70.42 | 1.83 |
| 12 | Compound 14 | 397 | 678 | 70.70 | 1.81 |
| 13 | Compound 15 | 399 | 681 | 70.73 | 1.80 |

As can be seen from the results, the glutamine derivative treatment groups exhibited an increase of 2.01%-8.9% in weight gain rate and a reduction of 5.18%-8.29% in feed coefficient as compared with the control group, indicating a significant improvement in feed efficiency.

Although specific examples have been used to illustrate and describe the present invention, it should be noted that many other changes and modifications can be made without departing from the spirit and scope of the present invention. Therefore, this means that all these changes and modifications that fall within the scope of the present invention are included in the appended claims.

The invention claimed is:

1. A method of improving animal production performance, wherein the method comprises administering an animal feed composition to an animal; and wherein the animal feed composition comprises a glutamine derivative having a structure of formula (I), a racemate thereof, a stereoisomer thereof, a geometric isomer thereof, a tautomer thereof, a solvate thereof, or a feed acceptable salt thereof; and an adjuvant suitable for feeds,

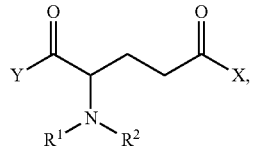

formula (I)

wherein, Y is a $C_1$-$C_{20}$ alkoxyl group or OH; X is a nitrogen-containing $C_4$-$C_{10}$ cycloalkyl group, a $NHC_1$-$C_{20}$ alkyl group, or a $N(C_1$-$C_{20}$ alkyl group$)_2$; $R^1$ is $R^{1a}C(=O)$, $R^{1b}C(=O)$, $R^{1a}S(=O)_2$, $R^{1b}S(=O)_2$, or H; and $R^2$ is $R^{2a}C(=O)$, $R^{2b}C(=O)$, $R^{2a}S(=O)_2$, or $R^{2b}S(=O)_2$;

$R^{1b}$ is a $C_1$-$C_{20}$ alkyl group or a $C_3$-$C_7$ cycloalkyl group, and $R^{2b}$ is a $C_3$-$C_7$ cycloalkyl group, wherein the $C_3$-$C_7$ cycloalkyl group is optionally substituted with one, two, three, four, or five $R^3$;

$R^3$ is —OH, —$NH_2$, —CN, —SH, or —$X_1$, wherein $X_1$ is selected from F, Cl, Br, or I;

each of $R^{1a}$ and $R^{2a}$ is independently a $C_6$-$C_{12}$ aryl group, a $C_5$-$C_{12}$ heteroaryl group, a —($C_1$-$C_4$ alkylidene)-$C_6$-$C_{12}$ heteroaryl group, or a —($C_1$-$C_4$ alkylidene)-$C_5$-$C_{12}$ heteroaryl group, wherein the $C_6$-$C_{12}$ aryl group, $C_5$-$C_{12}$ heteroaryl group, —($C_1$-$C_4$ alkylidene)-$C_6$-$C_{12}$ aryl group or —($C_1$-$C_4$ alkylidene)-$C_5$-$C_{12}$ heteroaryl group is optionally substituted with one, two, three, four, or five $R^4$; and $R^4$ is —OH, —$NH_2$, —$NO_2$, —CN, -SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

2. The method of claim 1, wherein $R^1$ is $R^{1a}C(=O)$ or H; $R^2$ is $R^{2a}C(=O)$; each of $R^{1a}$ and $R^{2a}$ is independently a $C_6$-$C_{12}$ aryl group, a $C_5$-$C_{12}$ heteroaryl group, a —($C_1$-$C_4$ alkylidene)-$C_6$-$C_{12}$ aryl group, or a —($C_1$-$C_4$ alkylidene)-$C_5$-$C_{12}$ heteroaryl group, wherein the $C_6$-$C_{12}$ aryl group, $C_5$-$C_{12}$ heteroaryl group, —($C_1$-$C_4$ alkylidene)-$C_6$-$C_{12}$ aryl group or —($C_1$-$C_4$ alkylidene)-$C_5$-$C_{12}$ heteroaryl group is optionally substituted with one, two, three, four, or five $R^4$; $R^4$ —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

3. The method of claim 1, wherein $R^1$ is H; $R^2$ is $R^{2a}C(=O)$; $R^{2a}$ is a $C_6$-$C_{12}$ aryl group or a —($C_1$-$C_4$ alkylidene)-$C_6$-$C_{12}$ aryl group, wherein the $C_6$-$C_{12}$ aryl group or —($C_1$-$C_4$ alkylidene)-$C_6$-$C_{12}$ aryl group is optionally substituted with one, two, three, four, or five $R^4$; and $R^4$ —OH, —$NH_2$, —$NO_2$, —CN, —SH, —$X_2$, —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

4. The method of claim 3, wherein $R^{2a}$ is a phenyl group or a —($C_1$-$C_4$ alkylidene)-phenyl group, wherein the phenyl group or —($C_1$-$C_4$ alkylidene)-phenyl group is optionally substituted with one, two, three, four, or five $R^4$; and $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

5. The method of claim 1, wherein $R^1$ is $R^{1b}C(=O)$ or H; $R^2$ is $R^{2b}C(=O)$; $R^{1b}$ is $C_1$-$C_{20}$ alkyl group or a $C_3$-$C_6$ cycloalkyl group, $R^{2b}$ is a $C_3$-$C_6$ cycloalkyl group, wherein the $C_1$-$C_{20}$ alkyl group or $C_3$-$C_6$ cycloalkyl group is optionally substituted with one, two, three, four, or five $R^3$; and $R^3$ —OH, —$NH_2$, —CN, —SH, or —$X_1$, wherein $X_1$ is selected from F, Cl, Br, or I.

6. The method of claim 1, wherein Y is a $C_1$-$C_{20}$ alkoxyl group.

7. The method of claim 1, wherein X is a nitrogen-containing $C_4$-$C_{10}$ cycloalkyl group.

8. The method of claim 1, wherein X is a $NHC_1$-$C_{20}$ alkyl group.

9. The method of claim 8, wherein X is a $NHC_1$-$C_{10}$ alkyl group.

10. A feed composition, wherein the feed composition comprises at least one of the glutamine derivative having a structure of formula (I), the racemate thereof, the stereoisomer thereof, the geometric isomer thereof, the tautomer thereof, the solvate thereof, and the feed acceptable salt thereof; and an adjuvant suitable for feeds,

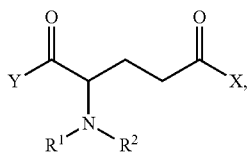

formula (I)

wherein Y is a $C_1$-$C_{20}$ alkoxyl group or OH; X is a nitrogen-containing $C_4$-$C_{10}$ cycloalkyl group, a $NHC_1$-$C_{20}$ alkyl group, or a $N(C_1$-$C_{20}$ alkyl group$)_2$; $R^1$ is $R^{1a}C(=O)$, $R^{1b}C(=O)$, $R^{1a}S(=O)_2$, $R^{1b}S(=O)_2$, or H; and $R^2$ is $R^{2a}C(=O)$, $R^{2b}C(=O)$, $R^{2a}S(=O)_2$, or $R^{2b}S(=O)_2$;

$R^{1b}$ is a $C_1$-$C_{20}$ alkyl group or a $C_3$-$C_7$ cycloalkyl group, and $R^{2b}$ is a $C_3$-$C_7$ cycloalkyl group, wherein the $C_3$-$C_7$ cycloalkyl group is optionally substituted with one, two, three, four, or five $R^3$;

$R^3$ is —OH, —$NH_2$, —CN, —SH, or —$X_1$, wherein $X_1$ is selected from F, Cl, Br, or I;

each of $R^{1a}$ and $R^{2a}$ is independently a $C_6$-$C_{12}$ aryl group, a $C_5$-$C_{12}$ heteroaryl group, a —($C_1$-$C_4$ alkylidene)-$C_6$-$C_{12}$ aryl group, or a —($C_1$-$C_4$ alkylidene)-$C_5$-C12 heteroaryl group, wherein the $C_6$-$C_{12}$ aryl group, $C_5$-$C_{12}$ heteroaryl group, —($C_1$-$C_4$ alkylidene)-$C_6$-$C_{12}$ aryl group or —($C_1$-$C_4$ alkylidene)-$C_5$-$C_{12}$ heteroaryl group is optionally substituted with one, two, three, four, or five $R^4$; and R is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

11. The feed composition according to claim 10, wherein the feed composition further comprises an additional animal feed additive, wherein the additional animal feed additive is selected from at least one of nutritive feed additives, general feed additives, and medicinal feed additives.

12. The feed composition according to claim 10, wherein the feed composition further comprises an animal feed raw material.

13. The feed composition of claim 10 for use in preparing an animal feed additive.

14. The feed composition according to claim 11, wherein the feed composition further comprises an animal feed raw material.

15. The feed composition of claim 11 for use in preparing an animal feed additive.

16. The feed composition of claim 10, wherein $R^1$ is $R^{1a}(=O)$ or H; $R^2$ $R^{2a}C(=O)$; each of $R^{1a}$ and $R^{2a}$ is independently a $C_6$-$C_{12}$ aryl group, a $C_5$-$C_{12}$ heteroaryl group, a —($C_1$-$C_4$ alkylidene)-$C_6$-$C_{12}$ aryl group, or a —($C_1$-$C_4$ alkylidene)-$C_5$-$C_{12}$ heteroaryl group, wherein the $C_6$-$C_{12}$ aryl group, $C_5$-$C_{12}$ heteroaryl group, —($C_1$-$C_4$ alkylidene)-$C_6$-$C_{12}$ aryl group or —($C_1$-$C_4$ alkylidene)-$C_5$-$C_{12}$ heteroaryl group is optionally substituted with one, two, three, four, or five $R^4$; $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

17. The feed composition of claim 10, wherein $R^1$ is H; $R^2$ is $R^{2a}C(=O)$; $R^{2a}$ is a $C_6$-$C_{12}$ aryl group or a —($C_1$-$C_4$ alkylidene)-$C_6$-$C_{12}$ aryl group, wherein the $C_6$-$C_{12}$ aryl group or —($C_1$-$C_4$ alkylidene)-$C_6$-$C_{12}$ aryl group is optionally substituted with one, two, three, four, or five $R^4$; and $R^4$ —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

18. The feed composition of claim 17, wherein $R^{2a}$ a phenyl group or a —($C_1$-$C_4$ alkylidene)-phenyl group, wherein the phenyl group or —($C_1$-$C_4$ alkylidene)-phenyl group is optionally substituted with one, two, three, four, or five $R^4$; and $R^4$ is —OH, —$NH_2$, —$NO_2$, —CN, —SH, —$X_2$, a —$C_1$-$C_5$ alkoxy group, a —$C_1$-$C_5$ alkyl group, or a —$C_1$-$C_5$ alkyl group substituted with $X_2$, wherein $X_2$ is selected from F, Cl, Br, or I.

19. The feed composition of claim 10 for use in preparing an animal feed.

20. The feed composition of claim 11 for use in preparing an animal feed.

* * * * *